US011457986B2

(12) United States Patent
Xu et al.

(10) Patent No.: US 11,457,986 B2
(45) Date of Patent: Oct. 4, 2022

(54) FORCE-FEEDBACK GLOVES FOR A SURGICAL ROBOTIC SYSTEM

(71) Applicant: Verb Surgical Inc., Santa Clara, CA (US)

(72) Inventors: Yiming Xu, Sunnyvale, CA (US); Berk Gonenc, Cupertino, CA (US); Blade Olson, Pasadena, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 73 days.

(21) Appl. No.: 17/039,705

(22) Filed: Sep. 30, 2020

(65) Prior Publication Data

US 2022/0096187 A1   Mar. 31, 2022

(51) Int. Cl.
*G09G 5/00* (2006.01)
*A61B 34/00* (2016.01)
*A61B 34/37* (2016.01)
*G06F 3/01* (2006.01)
*B25J 13/08* (2006.01)

(52) U.S. Cl.
CPC .............. *A61B 34/74* (2016.02); *A61B 34/37* (2016.02); *A61B 34/76* (2016.02); *B25J 13/08* (2013.01); *G06F 3/014* (2013.01); *G06F 3/016* (2013.01); *G06F 3/017* (2013.01); *A61B 2034/741* (2016.02)

(58) Field of Classification Search
CPC ... A61B 2034/741; A61B 34/37; A61B 34/74; A61B 34/76; B25J 13/08; G06F 3/011; G06F 3/014; G06F 3/016; G06F 3/017
See application file for complete search history.

(56) References Cited

U.S. PATENT DOCUMENTS

2016/0246370 A1\* 8/2016 Osman .................... G06F 3/014
2019/0377412 A1\* 12/2019 Parastegari ............. G06F 3/016

OTHER PUBLICATIONS

"DEXMO Development Kit 1 User Manual [V3.0] May 2019", Dexta Robotics Inc., 2017.

\* cited by examiner

*Primary Examiner* — Insa Sadio
(74) *Attorney, Agent, or Firm* — Womble Bond Dickinson (US) LLP

(57) ABSTRACT

A surgical robotic system that includes a robotic arm, glove configured to be worn on a hand of a user and including a force-feedback mechanism, a tracking device, a processor, and memory. The memory includes instructions which when executed by the processor causes the system to determine that the user is performing a hand gesture with the glove to grasp a virtual user input device (UID) based on the tracking device, and in response to the user grasping the virtual UID, apply, via the force-feedback mechanism, a force upon the glove that corresponds to a physical representation of the virtual UID, and engage the robotic arm to be controlled by the virtual UID.

20 Claims, 9 Drawing Sheets

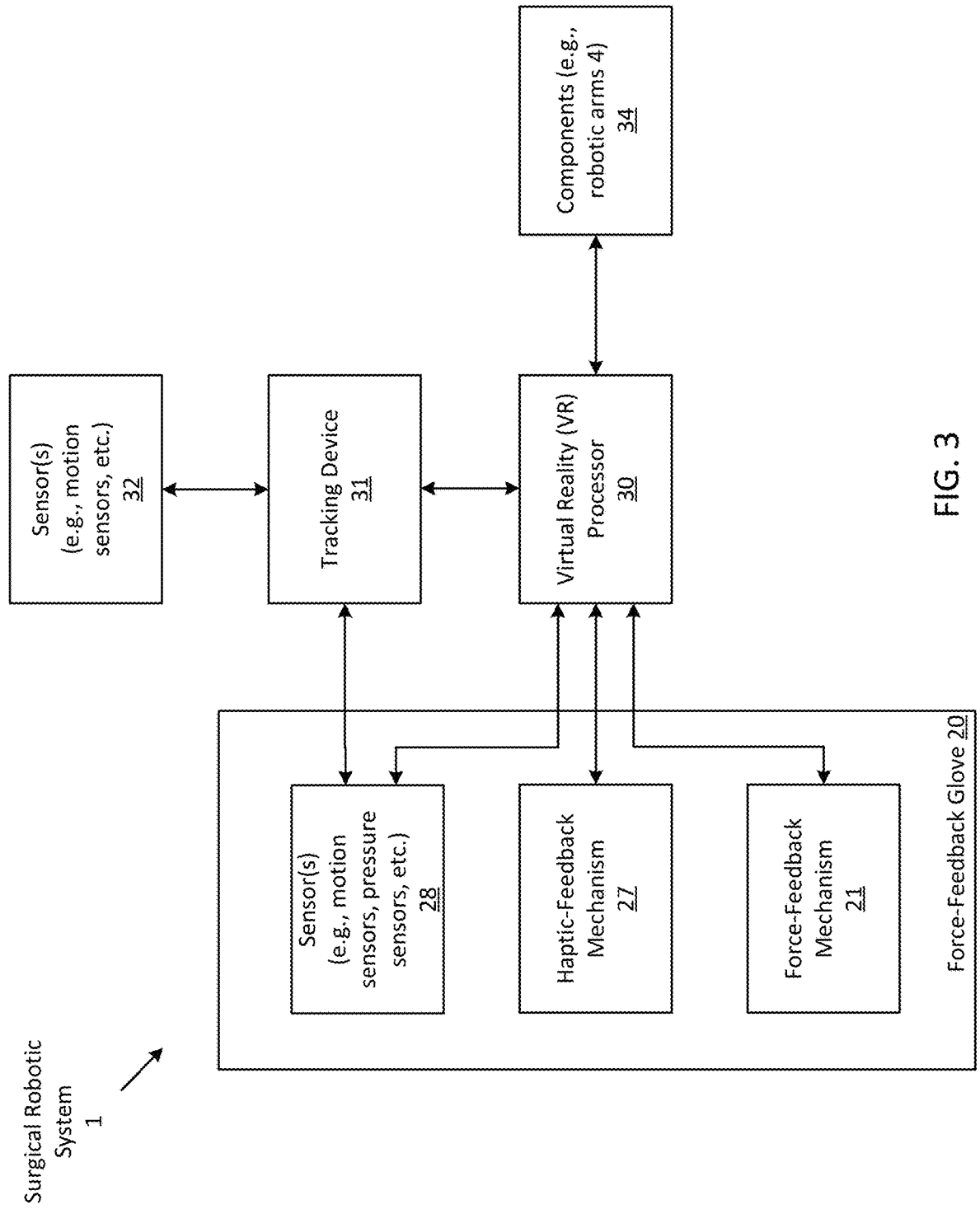

FORCE-FEEDBACK GLOVES FOR A SURGICAL ROBOTIC SYSTEM

FIELD

An embodiment of the disclosure relates generally to surgical robotic systems, and more specifically to a surgical robotic system that includes force-feedback gloves for providing intuitive control of a virtual user input device (UID). Other embodiments are also described.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one camera through the incisions into the patient. The surgical procedures can then be performed by using the introduced surgical tools, with the visualization aid provided by the camera.

Generally, MIS provides multiple benefits, such as reduced patient scarring, less patient pain, shorter patient recovery periods, and lower medical treatment costs associated with patient recovery. MIS can be performed with surgical robotic systems that include one or more robotic arms. A robotic arm may support at its distal end various devices such as surgical end effectors and imaging devices, and these are manipulated by the system based on commands from a remotely situated surgeon. The surgical robotic arm can thus assist the surgeon in performing surgery.

Control inputs from a user (e.g., surgeon or other operator) are captured via one or more user input devices and then translated into control of the robotic system. For example, in response to user commands, a tool driver having one or more motors may actuate one or more degrees of freedom of a surgical tool when the surgical tool is positioned at the surgical site in the patient.

SUMMARY

Surgical robotic systems may include input devices, such as (physical) user input devices (UIDs) that the system uses to control one or more components of the robotic system. A surgeon may perform a robotic surgery at a surgical station that includes a UID for controlling a robotic component of the system. To control the component, the surgeon may grasp the UID with one hand and manipulate the UID, and once the system has been placed into teleoperation mode control signals are generated and transmitted to the component. The control signals may control the component based on the user's manipulation of the UID. For instance, pressing a button on the UID may cause a robotic arm to perform a surgical task.

There are many types of UIDs. For example, there are "grounded" UIDs which are input devices that are mechanically tied or tethered (e.g., that are wired or coupled) to a control system. For example, grounded UIDs may be wired such that when (held and) manipulated by the user, the UID has a limited range of motion. There are also "floating" or "ungrounded" UIDs, which are input devices that are not mechanically tied or tethered to the control system. Such UIDs may include wireless input devices that are in wireless communication with the control system. Both types of UIDs have their respective advantages and disadvantages. For example, grounded UIDs may be robust against unintended engagement (e.g., activation of a robotic component) and/or disengagement (e.g., deactivation of the robotic component) and dropping incidents. For instance, grounded UIDs may have various mechanisms for engaging/disengaging robotic components, such as buttons, sliders, etc. Grounded UIDs prevent dropping incidents (which may inadvertently move a robotic component for which the UID controls) because these UIDs are able to independently hold their positions. Grounded UIDs, however, are limited in dexterity and freedom of motion because the devices are attached to robotic arms or gimbals which have their motion limitations and frictions. On the other hand, floating UIDs have an advantage in dexterity since the user can hold and move the UIDs in any manner so long as their positions and orientations are being tracked correctly by the system. For the same reasons that allow for the dexterity, however, the floating UIDs may be subject to unintended motions when the user forgets to disengage teleoperation and moves the UIDs unintentionally, or when the user drops the UIDs by accident. For instance, if the users were to drop (or release) the UID, the UID may transmit erroneous control signals (e.g., due to the motion of falling and/or the impact of the UID hitting the ground) to the system, thereby causing a robotic arm that is controlled by the UID to move unintentionally. Therefore, there is a need for a surgical robotic system in which an operator may control robotic components with a virtual UID that will increase user dexterity, as while as reduce (or prevent) the possibility of unintended motion and/or erroneous engagement/disengagement of the robotic components.

The present disclosure provides a force-feedback glove that enables intuitive and robust user-control of a surgical robotic system through the use of a virtual UID. In particular, the glove may include a force-feedback mechanism that is arranged to apply forces upon one or more of the user's fingers. The system may determine a virtual UID, such as a virtual joystick, which is configured to control a component (e.g., a robotic arm) of the surgical robotic system. For instance, the system may determine the virtual UID based on a user selection (e.g., via a user interface). The system may determine that the user is performing a hand gesture with the glove to grasp the virtual UID. For instance, the system may include a tracking device that is arranged to track hand gestures (e.g., using image data captured by one or more cameras). In response to the user grasping the virtual UID, the force-feedback mechanism may apply a force upon the glove that corresponds to a physical representation of the virtual UID. In other words, the applied force may provide the user a feeling as if the user's hand is holding a physical joystick. In addition, the system may engage the robotic arm to be controlled by the virtual UID, in response to the user grasping the virtual UID. If, however, the user was to perform another hand gesture to release the virtual UID (e.g., letting go of the virtual UID), the system would disengage the robotic arm.

Unlike conventional robotic systems in which an operator dawns a physical UID (e.g., a device that is held in the user's hand), the present disclosure provides a force-feedback glove, which when worn by the operator, simulates the physical UID through the use of force-feedback as the virtual UID. The glove gives the operator the impression of holding the physical UID (e.g., size, shape, texture, etc.), without actually having to dawn it. To control the robotic system, the user may manipulate the virtual UID by performing hand gestures with the glove, which may be similar or different to gestures that may be performed with a physical UID. Thus, the simulation of the virtual UID may inherently solve the engagement/disengagement and dropping issues of the grounded and floating UIDs.

The above summary does not include an exhaustive list of all embodiments of the disclosure. It is contemplated that the disclosure includes all systems and methods that can be practiced from all suitable combinations of the various embodiments summarized above, as well as those disclosed in the Detailed Description below and particularly pointed out in the claims. Such combinations may have particular advantages not specifically recited in the above summary.

BRIEF DESCRIPTION OF THE DRAWINGS

The embodiments are illustrated by way of example and not by way of limitation in the figures of the accompanying drawings in which like references indicate similar elements. It should be noted that references to "an" or "one" embodiment of this disclosure are not necessarily to the same embodiment, and they mean at least one. Also, in the interest of conciseness and reducing the total number of figures, a given figure may be used to illustrate the features of more than one embodiment, and not all elements in the figure may be required for a given embodiment.

FIG. 3 shows a block diagram of a surgical robotic system with the force-feedback glove according to one embodiment.

DETAILED DESCRIPTION

Several embodiments of the disclosure with reference to the appended drawings are now explained. Whenever the shapes, relative positions and other embodiments of the parts described in a given embodiment are not explicitly defined, the scope of the disclosure here is not limited only to the parts shown, which are meant merely for the purpose of illustration. Also, while numerous details are set forth, it is understood that some embodiments may be practiced without these details. In other instances, well-known circuits, structures, and techniques have not been shown in detail so as not to obscure the understanding of this description. Furthermore, unless the meaning is clearly to the contrary, all ranges set forth herein are deemed to be inclusive of each range's endpoints.

Figure 1:
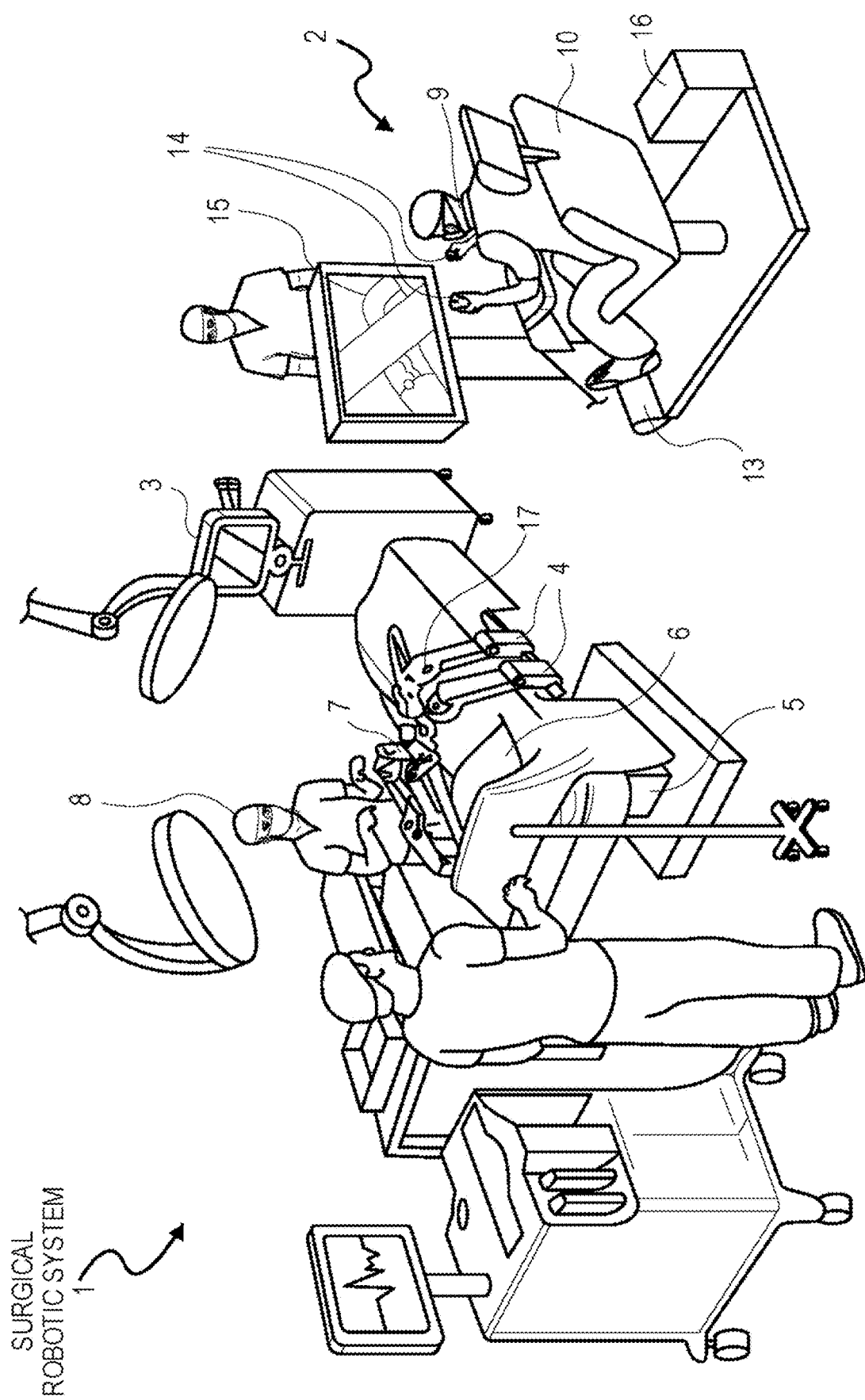
FIG. 1 shows a pictorial view of an example surgical robotic system in an operating arena.

FIG. 1 shows a pictorial view of an example surgical robotic system 1 in an operating arena. The robotic system 1 includes a user console 2, a control tower 3, and one or more surgical robotic arms 4 at a surgical robotic table (or surgical table) 5. In one embodiment, the arms 4 may be mounted to a table or bed on which the patient rests as shown in the example of FIG. 1, or they may be mounted to a cart separate from the table or bed. In one embodiment, at least some of the arms 4 may be configured differently. For example, at least some of the arms may be mounted on a ceiling, sidewall, or in another suitable structural support. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached.

Generally, a remote operator 9, such as a surgeon or other operator, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices (handheld UIDs) 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilising the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilisation and healthcare record entry or printout via the user console 2.

In one embodiment, the remote operator 9 holds and moves the UID 14 to provide an input command to move a robot arm actuator 17 (or driving mechanism) in the robotic system 1. The UID 14 may be communicatively coupled to the rest of the robotic system 1, e.g., via a console computer system 16 (or host). The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 or driving mechanism may include one or more actuators and/or one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, which opens or closes jaws of the grasper at a distal end of surgical tool 7 to grip tissue within patient 6.

In some embodiments, the communication between the surgical robotic table 5 and the user console 2 may be through a control tower 3, which may translate user commands that are received from the user console 2 (and more particularly from the console computer system 16) into robotic control commands that transmitted to the arms 4 on the surgical table 5. The control tower 3 may also transmit status and feedback from the surgical table 5 back to the user console 2. The communication connections between the surgical table 5, the user console 2, and the control tower 3 may be via wired (e.g., optical fiber) and/or wireless links, using any suitable ones of a variety of data communication protocols, such as BLUETOOTH protocol. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 2A:
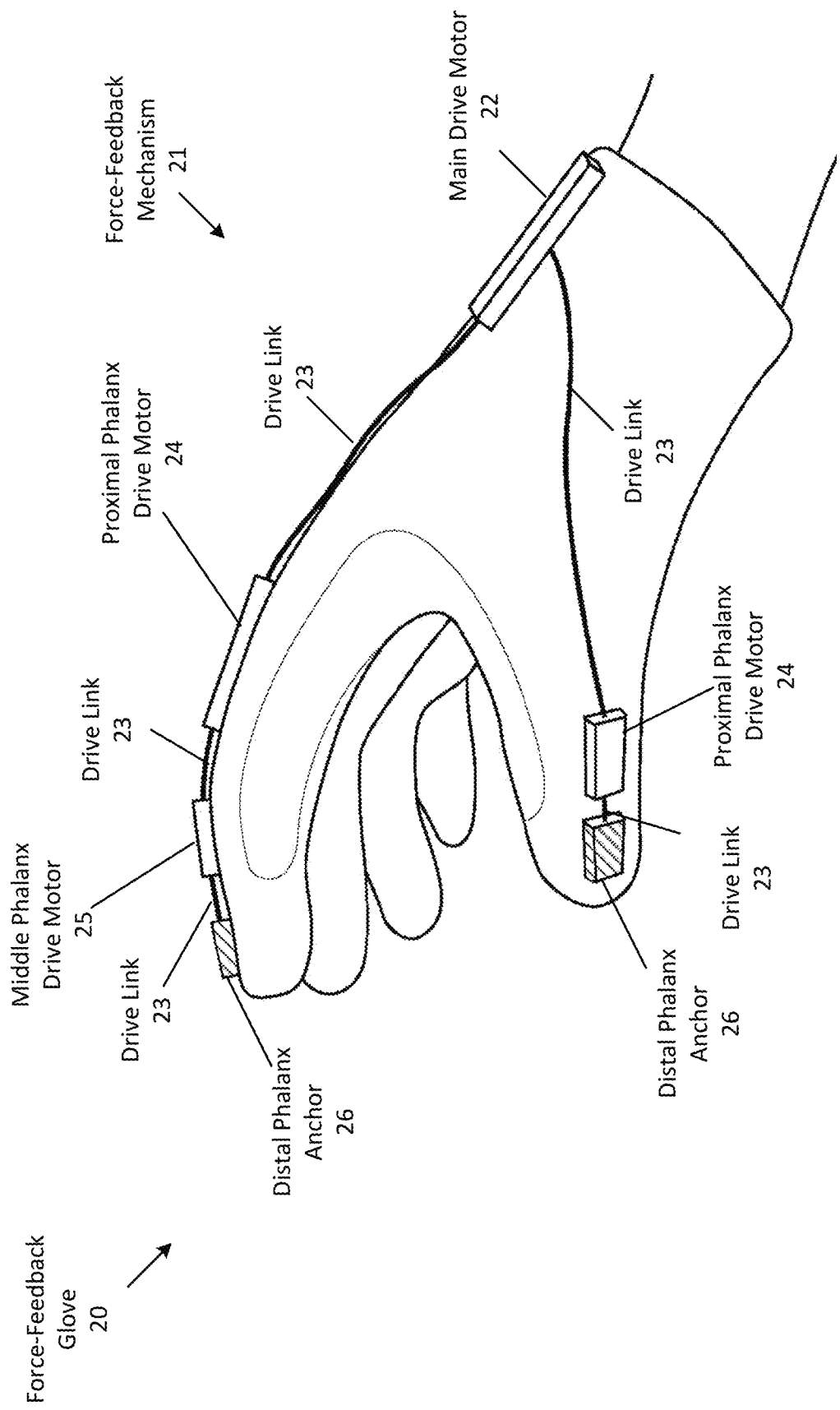
FIGS. 2A and 2B show different views of a force-feedback glove of the surgical robotic system according to one embodiment.
Figure 2B:
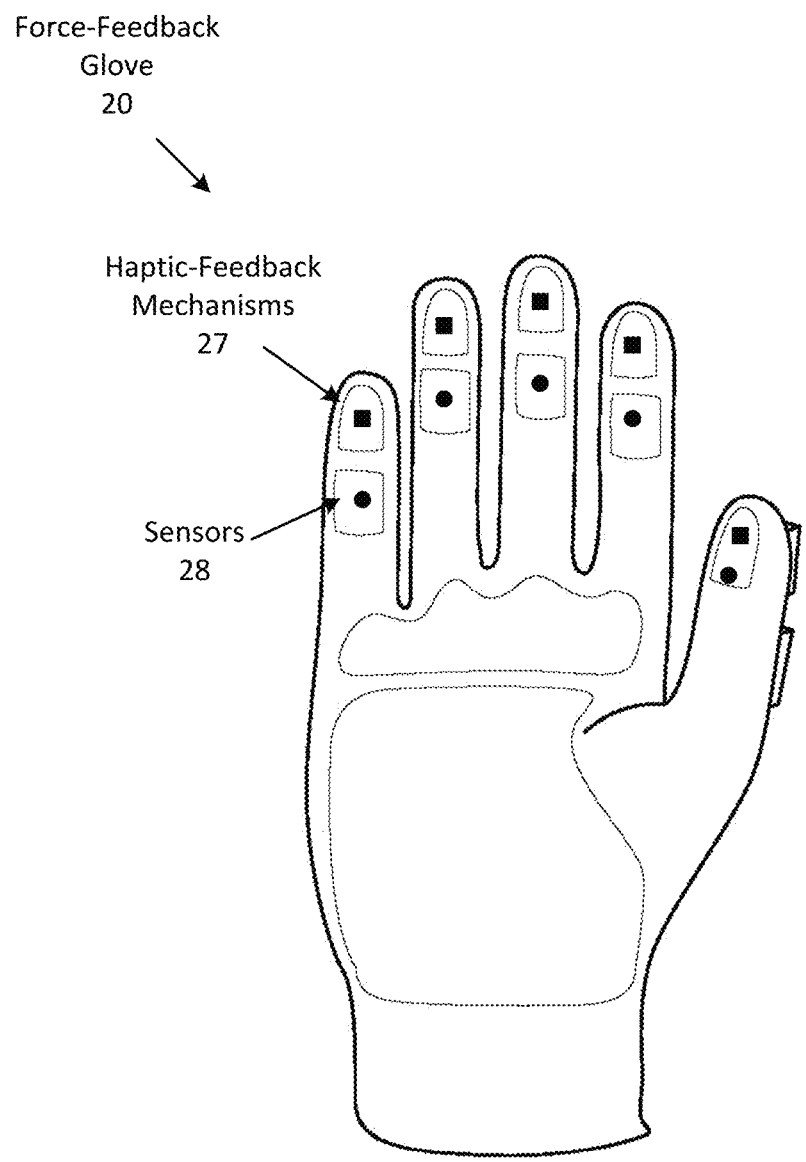

FIGS. 2A and 2B show different views of a force-feedback glove 20 of the surgical robotic system 1 according to one embodiment. The force-feedback glove (which may be referred to as glove) may be configured to allow a user who is wearing the glove to feel the shape, size, and texture of a virtual object. As described herein, the glove may provide a user the ability to control of one or more components (e.g., robotic arm 4) of the surgical robotic system 1 through manipulation of a virtual user input device (UID), which is in contrast to conventional surgical systems in which the operator controls the system via one or more physical UIDs.

FIG. 2A illustrates a side (or lateral) view of the force-feedback glove 20, which includes a force-feedback mechanism 21 that is arranged to apply one or more forces to reduce or prevent movement of one or more portions of the user's hand (when the glove is worn by the user) in order to provide the user a feeling of grasping (holding) or touching an object that is not in the physical space. For instance, the mechanism may be arranged to reduce movement of at least one finger or thumb of the glove 20, thereby limiting movement of a user's corresponding finger or thumb in order to provide a feeling of a physical representation of a virtual UID, as described herein.

As used herein, a thumb may be referred to as a finger hereafter. Thus, in this description the phrase "fingers" may refer to at least one of four fingers or may refer to at least one of the four fingers and the thumb.

As show, the mechanism includes a main drive motor 22, one or more proximal phalanx drive motors 24, one or more middle phalanx driver motors 25, and one or more distal phalanx anchors 26. In one embodiment, each of the drive motors may include a driving mechanism (e.g., a motor, an actuator, etc.) that is arranged to receive one or more control signals (as electrical signals), and is arranged pull (and release) a distally coupled drive link 23 based on the received control signals. In some embodiments, the motors may include one or more driving mechanisms. For example, the main drive motor 22 may include at least five actuators, one for each finger.

As shown, the thumb of the glove includes a proximal phalanx drive motor 24 and a distal phalanx anchor 26, and each of the four fingers of the glove includes a proximal phalanx drive motor 24, a middle phalanx drive motor 25, and a distal phalanx anchor 26. Each of the proximal phalanx drive motors 24 is coupled to the main drive motor 22 via a drive link 23. For the thumb, the anchor 26 is coupled to drive motor 24 via a drive link 23. For each of the fingers, an anchor 26 is coupled to a drive motor 25 via a drive link 23, and the drive motor 25 is coupled to drive motor 24 via another drive link 23. In one embodiment, each of the phalanx driver motors and anchors may be positioned along the glove such that while a user's hand is in the glove a portion of the user's hand is proximate to (e.g., in contact with) or coupled to a correspondingly named motor or anchor of the force-feedback mechanism. For example, while the user is wearing the glove 20, a proximal phalanx drive motor 24 may be in contact with each of the proximal phalanges of the user's hand, a middle phalanx drive motor 25 may be in contact with each of the four middle phalanges of the user's hand, and a distal phalanx anchor 26 may be in contact with each of the distal phalanges of the user's hand. In one embodiment, each of the anchors may be structures that couple a drive link to a corresponding distal phalanx (or a portion of the glove 20 at which the distal phalanx is positioned while the user is wearing the glove.

Each of the driver motors (e.g., motors 22, 24, and/or 25) may be arranged to apply a (e.g., pulling) force upon a drive link that is distally coupled to the corresponding drive motor according to one or more control signals. Specifically, each of the drive motors may apply a pulling force that pulls a corresponding distally coupled drive link in a proximal direction in order to reduce or prevent movement of at least a portion of the user's hand. For example, the main drive motor 22 may apply a pulling force upon a drive link 23 that is coupled to the proximal phalanx drive motor 24 of the index finger of the glove. This pulling effectively reduces or prevents movement of the user's index finger, specifically limiting movement of the proximal phalanx about the metacarpophalangeal joint. Although movement about the metacarpophalangeal joint may be reduced, a remainder of the user's index finger may continue to have at least some range of motion. In one embodiment, the range of motion may be further limited. For instance, the proximal phalanx drive motor 24 may apply a pulling force upon the drive link that is coupled to the middle phalanx drive motor 25 in order to reduce or prevent movement of the middle phalanx about the interphalangeal joint that couples the middle phalanx to the proximal phalanx. Finally, movement of the distal phalanx about the interphalangeal joint (which couples the middle phalanx to the middle phalanx) may be reduced as a result of the drive motor 25 applying a pulling force that pulls the drive link that couples the distal phalanx anchor 26 to the drive motor 25. In one embodiment, each of the motors may be independently controlled, and/or each of the motors may apply a same (similar) or different pulling force, according to one or more control signals.

In one embodiment, the drive links 23 are structures that are arranged to move proximally and distally based on a pulling (or pushing) force that may be applied by one or more drive motors. For instance, the drive links may include pliable (e.g., flexible) structures (e.g. wire, cord, etc.) that may be pulled and released by the drive motors. In another embodiment, the drive links may include one or more rigid structures composed of any material (e.g., steel, plastic, etc.). In this case, the rigid structures may house one or more cords or wires that is used to apply the pulling force. In another embodiment, the drive motors may apply the pulling force upon the one or more rigid structures of the drive links in order to reduce or prevent movement as described herein. In one embodiment, the drive links may include one or more joints about which one or more rigid structures are rotatably coupled.

As shown herein, the components of the force-feedback mechanism 21 may be (removably) coupled or attached to the (e.g., dorsal side of the) glove 20. For example, each of the components may be attached to the glove, such that when the glove is removed from a user's hand, the components remain on the glove. As another example, at least some of the components may be arranged to directly couple to a user's hand. For instance, the distal phalanx anchor 26 may include a clip or strap that may be wrapped around at least a portion of the user's finger (e.g., the distal phalanx). In one embodiment, the glove may be composed of any material (e.g., cloth, nylon, plastic etc.), and may be at least partially flexible in order to allow a user who is wearing the glove to make hand gestures, as described herein.

In one embodiment, the force-feedback mechanism 21 may include less or more components. Specifically, the mechanism may include less drive motors and/or drive links. For example, the mechanism may not include middle and proximal phalanx drive motors. As a result, the main drive motor 22 may couple to a distal phalanx anchor 26 (for each finger) via a drive link 23.

In another embodiment, the force-feedback mechanism may include more driver motors and/or drive links. For instance, the mechanism may include one or more driver motors disposed on a dorsal portion of the glove. In this case, at least one driver motor may be coupled between at least one drive motor 24 and the main drive motor 22. As described and illustrated herein, each of the components of the mechanism are disposed on a dorsal side of the glove 20. In some embodiments, the palmar side of the glove may include at least some components such that the mechanism may apply forces upon the palmar side and the dorsal side of the glove.

FIG. 2B illustrates a palmar (or ventral) view of the force-feedback glove 20. From this view, it is illustrated that the glove includes one or more haptic-feedback mechanisms 27 (e.g., as black squares) and one or more sensors 28 (e.g., as black circles). Specifically, each finger of the glove includes a haptic-feedback mechanism and a sensor. In one embodiment, each finger may include more or less mechanisms and/or sensors. In another embodiment, mechanisms and/or sensors may be disposed at other locations about the glove (e.g., on the palm, etc.). In one embodiment, at least some of the mechanisms and sensors may be integrated within (e.g., the material of) the glove 20. In some embodiments, they may be coupled to an external surface of the glove, and/or may be coupled to an internal surface of the glove such that the element comes into contact with the user's hand while the user is wearing the glove. In one embodiment, the glove may include more or less mechanisms and sensors, which may be positioned anywhere about the glove. For example, as illustrated a sensor is positioned on the palmar side of the glove. Sensors, however, may be positioned elsewhere, such as on the dorsal side of the glove.

In one embodiment, the haptic-feedback mechanisms 27 may be arranged to create a sense of touch or movement for a virtual object, such as the virtual UID. Specifically, each mechanism may apply one or more forces that represent physical characteristics, such as a surface and texture, of a physical representation of the virtual object. In one embodiment, the mechanism may include a motor or actuator that is configured to receive control signals and are configured to apply forces, vibrations, and/or motions according to the control signals. In another embodiment, each of the mechanisms may be independently controlled. As a result, when grasping a virtual object, the force-feedback mechanism 21 provides the user with a sense of the shape and size of the object, while the haptic-feedback mechanism provides for the objects texture and feel.

The sensors 28 may be any type of sensors that are arranged to sense (or detect) finger and/or hand motions perform by the user and arranged to generate sensor data (e.g., as electrical signals) that indicates the sensed motions. A finger motion may include movement of a particular finger with respect to the glove as a whole, such as when an index finger bends at the metacarpophalangeal joint. A hand motion may include movement of the whole hand with respect to a separate reference point, such as when a hand pans from left to right. In one embodiment, the system may use the sensor data to determine whether the user is performing a specific hand gesture. For example, sensor data that indicates that each of the fingers are moving in one direction, while the thumb is moving in another direction may represent that the user is performing a grasping hand gesture. More about hand gestures is described herein.

In one embodiment, the sensors 28 may include motion (and orientation) sensors, such inertia motion units (IMUs), passive infrared sensors (PIRs), ultrasonic sensors, etc. In another embodiment, one or more of the sensors may include pressure (or force) sensors that are arranged to sense an applied force. For example, the pressure sensor may be a strain gauge that is detecting for strain or deformations in the material of the glove that are caused by finger and/or hand motions (e.g., clenching a fist, moving fingers, etc.). Thus, sensor data from the pressure sensors may be used to determine motion based on stretching and relaxing of the glove material. In another embodiment, pressure sensors may be disposed on the force-feedback mechanism 21 to detect force being applied by the user, while the mechanism is active (e.g., applying a pulling force as described herein). In one embodiment, the pressure sensors may be arranged to sense pressure being applied onto the sensor by the user (e.g., by pressing against the sensor). For instance, a pressure sensor on the index finger (and/or the thumb) may be used to sense how much pressure is being applied when the user is performing a pinching hand gesture. In another embodiment, the sensors may include proximity sensors that are arranged to sense the presence (and distance) of nearby objects, such as capacitive sensors, inductive sensors, and optical sensors. From sensor data produced by proximity sensors, the system may determine finger and/or hand motion.

FIG. 3 shows a block diagram of the surgical robotic system 1 with the force-feedback glove 20 according to one embodiment. Specifically, the system is configured to provide intuitive control of a virtual UID by using the force-feedback glove 20, thereby allowing a user who is wearing the glove to control a component (e.g., robotic arm 4) of the system that is associated with the virtual UID. As illustrated, the block diagram includes several elements, such as the force-feedback glove 20, one or more virtual reality (VR) processors 30, a tracking device (system or subsystem) 31, one or more sensors 32, and one or more components 34 of the surgical robotic system (e.g., a robotic arm 4). In one embodiment, the VR processor and the tracking device may each perform one or more operations, which may be implemented (e.g., as software) as one or more programmed processors (generically referred to here as "a processor that is to execute instructions stored in memory). In one embodiment, the VR processor and the tracking device may be implemented within a computing system that is local to the user, such as the console computer 16, shown in FIG. 1. In another embodiment, the operations described herein may be implemented in one or more local computer and/or one or more remote computers (e.g., servers) over a network (e.g., the Internet).

In one embodiment, the force-feedback glove 20 may be communicatively coupled to the VR processor 30 and the tracking device 31 in order to receive control signals and transmit sensor data, as described herein. For instance, when the VR processor and tracking device are implemented in a local computer, such as the console computer 16, the glove may be configured to establish a wireless connection with the console computer via any wireless communication protocol (e.g., BLUETOOTH protocol). During the established connection, the glove may exchange (e.g., transmit and receive) data packets (e.g., Internet Protocol (IP) packets) with the computer, which include sensor data, control signals, and/or spatial state signals. In another embodiment, the glove may be coupled to the VR processor and the tracking device via a wired connection. In some embodiments, the VR processor and/or tracking device may be a part of (or integrated with) the glove.

The components 34 may be any components that are associated with the surgical robotic system 1, such as the robotic arms 4, tools 7 (e.g., a grasper), and the user display 15. In one embodiment, components may include software that may be executing on one or more processors of the surgical robotic system (e.g., executed by the console computer 16). For instance, a component may include a user interface (UI) that is displayed on the user display 15. As another example, components may include device settings of one or more devices, such as a light dimmer or a volume control.

The sensors 32 may be any type of sensors that are arranged to sense motion (e.g., motion of the force-feedback glove 20), and arranged to generate sensor data that indicates the sensed motion. In one embodiment, sensors 32 may be the same or similar to sensors 28 of the force-feedback glove 20. For example, sensors 32 may be motion sensors, such as optical motion sensors (e.g., PIRs) and ultrasonic sensors. In another embodiment, the sensors may include other sensors, such as one or more cameras that are arranged to capture image data of a scene within a field of view of the camera as one or more images. In some embodiments, the sensors 32 may be a part of one or more electronic devices and/or may be stand-alone electronic devices (e.g., a stand-alone camera). For instance, one or more sensors may be a part of a component of the user console 2, such as the seat 10 or user display 15, as illustrated in FIG. 1.

The tracking device 31 is configured to obtain sensor data from sensors 38 and/or sensors 32, and is configured to determine whether the user is performing a hand gesture with the force-feedback glove 20 according to the sensor data. Specifically, the tracking device may keep track of a position and an orientation of the glove, and determine whether any portion of the glove changes its position with respect to the glove as a whole and/or whether the glove changes its position and orientation within the physical space (e.g., with respect to a reference point). Once a change is identified (e.g., based on sensor data, which may for example indicate that the index finger and the thumb are moving towards one another), the tracking device may determine a particular hand gesture associated with such a change. In one embodiment, the tracking device may determine hand gestures based on changes in finger and/or hand motions with machine learning and/or a trained neural network. In another embodiment, the tracking device may perform a table lookup into a data structure that associates hand gestures with finger and/or hand motions indicated by the sensor data. Returning to the previous example, the tracking device may determine that the user is performing a pinching hand gesture based on the identified movement of the index finger and thumb.

In one embodiment, the tracking device may perform an image recognition algorithm to determine whether the user is performing a hand gesture. For instance, the system may obtain image data from one or more cameras, as described herein. Using the image data, the system may perform image recognition to identify finger and/or hand motions. Once identified, the system may determine a hand gesture associated with the motions, as described herein. More about the tracking device 31 is described herein.

The VR processor 30 is configured to provide a virtual surgical robotic environment that may include one or more virtual UIDs that are configured to control one or more robotic components of the surgical robotic system in response to user manipulation of the virtual UIDs via the force-feedback glove 20. As described herein, the virtual surgical robotic environment may serve as a useful tool with respect to robotic surgery, in applications including but not limited to performing a surgical procedure, training, simulation, and/or collaboration among multiple persons.

Generally, the VR processor 30 is configured to generate the virtual robotic surgical environment in which a user may interact with one or more virtual objects (e.g., virtual UIDs) via the force-feedback glove in order to control robotic components of the system. The user may interact with the virtual UIDs by moving and/or manipulating the glove 20, as if the user were manipulating a physical UID. For example, the user may select (e.g., via a user interface) a virtual UID that is associated with a particular robotic component, which the VR processor simulates. To interact with the virtual UID, the user may perform a hand gesture with the glove as if to grasp or hold a physical version of the object. This gesture is detected by the VR processor, which then configures the glove to provide force-feedback to provide the user with the impression as if holding the actual object. Thus, user may interact with the virtual UID as if interacting with the physical UID. For example, the virtual UID may include one or more virtual buttons, triggers, scroll wheels, switches, and/or other suitable interactive features that the user may manipulate to interact. When user input is received (e.g., by selecting a virtual button), the VR processor may generate and transmit a control signal to the robotic component associated with the virtual UID to manipulate the robotic component.

In one embodiment, as described herein, the VR processor may also be configured to generate a visual representation of the virtual robotic surgical environment via a display (e.g., display 15) and/or a head-mounted display (HMD).

determine whether a user is manipulating a virtual UID that is associated with a component of the surgical robotic system with the force-feedback glove 20, and is configured to control the component according to the user-manipulation. Thus, the virtual UID allows a user to control a component of the surgical robotic system without having to hold and manipulate a physical UID. In addition, while manipulating the virtual UID, the force-feedback glove 20 is arranged to provide haptic and force-feedback in order to provide a natural and intuitive way to control the component without the disadvantages of motion restrictions from a grounded device or the unintended motion risks from a floating device. More about the operations performed by the VR processor is described herein.

Figure 4:
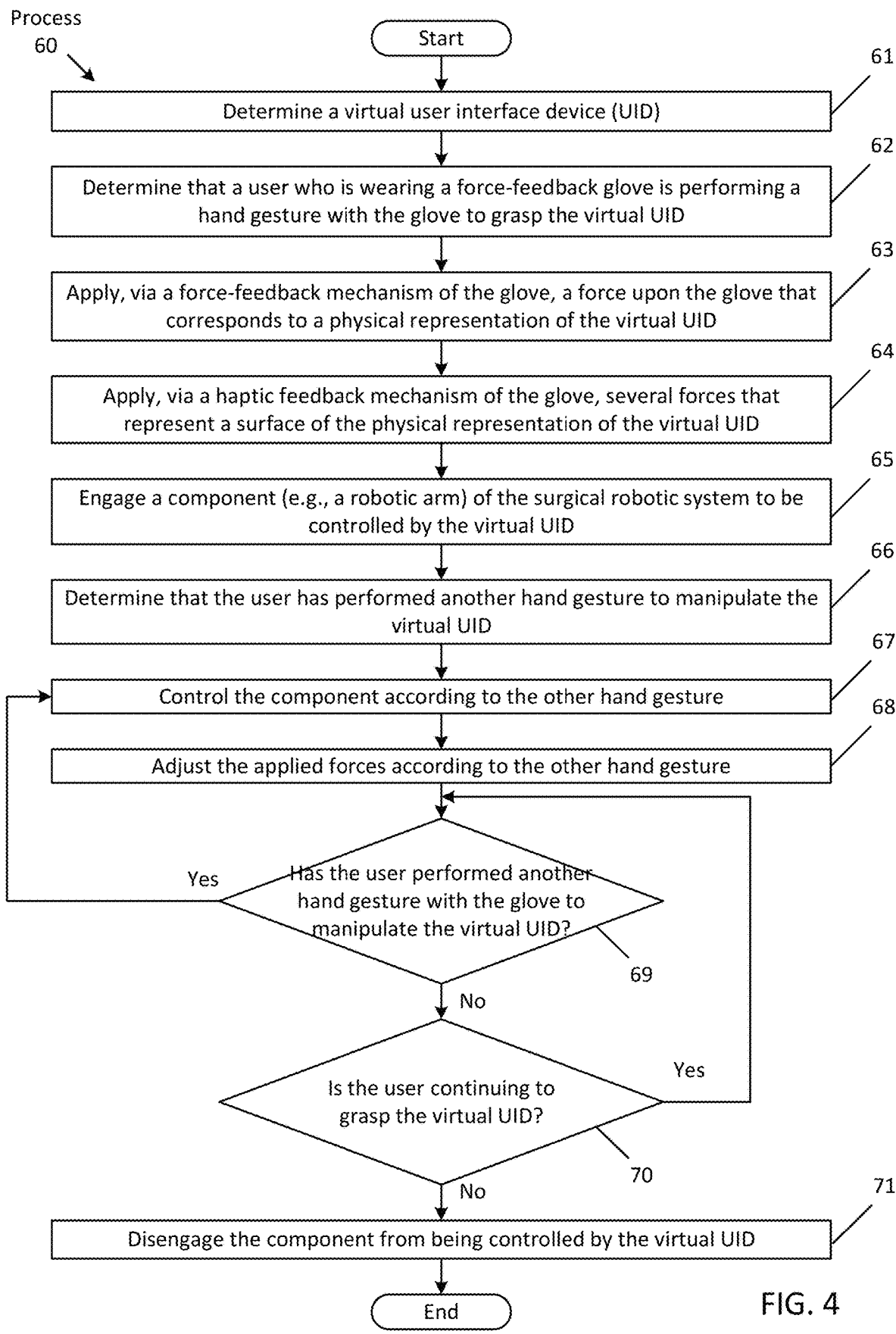
FIG. 4 is a flowchart of a process to use the force-feedback glove to engage a component of the surgical robotic system with a virtual user input device (UID) and to manipulate the virtual UID in order to control the component according to one embodiment.

FIG. 4 is a flowchart of a process to use the force-feedback glove 20 to engage a component of the surgical robotic system with a virtual UID and to manipulate the virtual UID in order to control the component according to one embodiment. In one embodiment the process 60 may be performed by the surgical robotic system 1. Specifically, at least a portion of the process may be performed by any of the components, such as the VR processor 30 and tracking device 31 of the system 1. Accordingly, this figure will be described with reference to FIGS. 1-3. The process 60 begins by determining a virtual UID (at block 61). The VR processor 30 may be configured to determine (or produce) one or more virtual objects, such as virtual UIDs by retrieving virtual UID characteristic data from memory of the system 1. In one embodiment, the processor may retrieve the data from a remote location (e.g., from a remote server via a network). The data may indicate physical characteristics of the virtual UID, such as shape, size, texture, and firmness. In one embodiment, the data may indicate characteristics of different portions of the virtual UID, such as whether one portion of the UID is firmer (or more stiff) than another portion of the UID. The data may also indicate whether the UID is associated with one or more robotic components of the surgical robotic system, such as a robotic arm. In one embodiment, the determination of the virtual UID may be based on a user input. The system 1 may obtain user input (e.g., a user-selection of the virtual UID via an input device, such as a touchscreen, a keyboard, etc.) that indicates a particular virtual UID the user wishes to hold and manipulate during a surgical procedure. In one embodiment, the system may also obtain user input that indicates a particular component the user wishes to control. In response, the system may determine one or more virtual UIDs that are associated with the particular component. For instance, the user may select to control a robotic arm with a joystick. In which case, the VR processor may retrieve virtual UID characteristic data of a virtual joystick that describes the shape, size, and texture of a joystick.

In one embodiment, the virtual UID may be a virtual representation of any type of input device that is arranged to control a component of the surgical robotic system. For instance, the virtual UID may be a joystick, a mouse, a keyboard, etc. In another embodiment, the virtual UID may have any shape and size. In some embodiments, virtual UIDs may be predefined (e.g., by a manufacturer), or may be user-defined (stored in the data structure described herein). For example, a user may define physical characteristics (e.g., shape, size, and texture) of the virtual UID and/or may define the functionality of the virtual UID (e.g., via an input device of the surgical robotic system). In particular, the user may associate the virtual UID with a particular component, along with defining the virtual UID's capabilities that control the functionality of the particular component. For example, the user may define inputs (e.g., buttons, sliders, etc.) of the virtual UID, and define which functionalities of the component are controlled by the inputs. As an example, when the virtual UID is associated with a mechanical grasper with a grasping mechanism, the user may define squeezing the virtual UID as controlling the grasping mechanism (e.g., squeezing the UID may cause the grasper to grasp an object, while releasing the UID may cause the grasper to release the object). As another example, the user may define a button for controlling that same function.

In one embodiment, the VR processor 30 is configured to determine (or define) a location for the virtual UID within the physical space in which the user is located. Specifically, the VR processor 30 may use the virtual UID's characteristic data to define a physical representation of the virtual UID in order to position the virtual UID within the space. For instance, when the virtual UID is a virtual joystick, the VR processor may define the shape, size, texture of the virtual joystick based on the characteristic data. Once defined, the VR processor may position the virtual UID at a location within the physical space. In one embodiment, the VR processor may define the location the VR processor by producing a three-dimensional (3D) coordinate system that corresponds to the physical space, and place the virtual UID within the system. Once defined, the VR processor may define the shape and size of (the physical representation of) the virtual UID within the 3D system, according to the characteristic data. In one embodiment, the VR processor may position the virtual UID within the physical space at a predefined location. In another embodiment, the VR processor may position the virtual UID with respect to the user (e.g., positioned in front of and to the left of the user). In some embodiments, the virtual UID may be positioned with respect to a position and orientation of the force-feedback glove 20. Specifically, the VR processor may obtain the position and orientation of the glove from the tracking device 31, and position the virtual UID at a location with respect to the glove. For example, the VR processor may position the virtual UID at a location proximate to a palmar side of the glove, such that the user may grasp and manipulate the virtual UID. In one embodiment, the virtual UID may be stationary with respect to the glove such that the virtual UID mirrors movements of the glove within the physical space. In other words, when the glove moves within the physical space (e.g., the user pans the hand wearing the glove from left to right), the virtual UID moves with the glove. In this case, the UID may move without being held (or grasped) by the user.

The process 60 determines that a user who is wearing the force-feedback glove is performing a hand gesture with the glove to grasp the virtual UID based on the tracking device (at block 62). In one embodiment, to "grasp" may relate to a hand gesture in which at least a portion of the glove is to be positioned within the physical space as if to touch the physical representation of the virtual UID. In another embodiment, grasping relates to at least two fingers of the glove being positioned such that they are touching (or holding) the physical representation of the virtual UID. Specifically, the tracking device 31 obtains sensor data from one or more sensors that indicates finger and/or hand motion by the glove, and determines that the user is performing the hand gesture according to those movements, as described herein. The VR processor determines whether the hand gesture may result in the user grasping the virtual UID. In particular, the VR processor determines the position of the virtual UID in the physical space (as defined by the VR processor), the position of the glove, and determines whether the performance of the hand gesture results in the glove grasping the (e.g., physical representation of the) virtual UID.

The process 60 applies, via the force-feedback mechanism 27 of the glove 20, a force upon the glove that corresponds to the physical representation of the virtual UID (at block 63). In particular, the VR processor 30 may determine what portions of the glove are coming into contact with the virtual UID. For instance, the VR processor may determine that the index finger and thumb are coming into contact with the virtual UID when the hand gesture is a pinching gesture. The VR processor may also determine what portions of the virtual UID are being touched by the glove. Knowing what portions of the glove are coming into contact with the virtual UID, the VR processor is configured to produce (generate) one or more control signals for controlling the force-feedback mechanism 21. For instance, continuing with the previous example, when the hand gesture is a pinching gesture with the index finger and thumb, the VR processor may generate control signals to control the main drive motor 22 and/or one or more drive motors 24 and 25 of the mechanism 21 to reduce or prevent movement of the index finger and thumb of the glove 20. Specifically, the control signals may define an amount of pulling force that one or more motors of the force-feedback mechanism is to apply to one or more drive links 23. The VR processor is to transmit the control signals to the force-feedback mechanism of the glove, which then applies the force as described herein. In one embodiment, the amount of force determined by the VR processor that is to be applied may be predefined (e.g., such that the portions of the glove coming into contact with the virtual object are prevented from bending or moving into an outer boundary of the virtual UID). In another embodiment, the force may be based on the portions of the virtual UID that are in contact with the glove. For instance, the VR processor may determine that the portions of the virtual UID are not firm (or pliable) based on the UID's characteristics data. As a result, the VR processor may generate control signals that cause the force-feedback mechanism to reduce or prevent movement of the glove, up to a threshold opposite force being applied by the user's hand (e.g., while performing the pinching or squeezing hand gesture). Once the threshold is met, the force-feedback mechanism may reduce the applied force to allow the portions of the glove to move into the virtual UID (thereby squeezing the virtual UID).

The process 60 applies, via a haptic feedback mechanism of the glove, several forces that represent a surface of the physical representation of the virtual UID (at block 64). Specifically, the VR processor 30 may determine which forces to be applied based on characteristics data (e.g., texture) associated with the portions of the virtual UID that are being grasped by the user. Once determined, the VR processor 30 produces control signals that indicate the amount of force to be applied by one or more haptic-feedback mechanism 27 of the glove, and the processor transmits the control signals to the mechanism 27. For instance, continuing with the previous example in which the glove is performing a pinching hand gesture, the VR processor may produce control signals to cause the haptic-feedback mechanisms 27 of the index finger and thumb to apply one or more forces to represent the surface (and texture) of the physical representation of the virtual UID.

The process 60 engages a component of the surgical robotic system to be controlled by the virtual UID (at block 65). Specifically, as described herein, the virtual UID may be associated with one more ore components, such as a robotic arm 4. The VR processor 30 is configured to engage the component by activating the component such that the component becomes configured to receive control signals for controlling the component. As described herein, such control signals may be produced by the system in response to the user manipulating the virtual UID. In one embodiment, the VR processor may engage the component by transmitting an engagement signal to one or more controllers, indicating that the component is to be controlled by the user. In one embodiment, the VR processor engages the component in response to the determination that the user is performing the hand gesture with the glove to grasp (or touch) the virtual UID. In another embodiment, different hand gestures may engage different virtual UIDs. For example, grasping one virtual UID with (at least) three fingers may engage an associated component, while grasping another virtual UID with (at least) two fingers may engage its associated component.

In one embodiment, the system may wait for a period of time (e.g., five seconds) before engaging the component. This may allow the user to prepare for controlling the component. In another embodiment, the system may alert the user that the component is to be engaged. For instance, the system may display an alert message on the user display screen 15 (e.g., "The Robotic Arm has been Engaged"). In yet another embodiment, the system may cause the haptic-feedback mechanism to provide a haptic feedback alert (e.g., pulsing vibrations) in order to alert the user that the component is being engaged.

The process 60 determines that the user has performed another hand gesture to manipulate the virtual UID (at block 66). Specifically, sensor data produced by one or more sensors (e.g., sensors 28 and/or sensors 32) may indicate that the glove is manipulating the virtual UID. For example, one or more pressure sensors may produce sensor data that indicates that the user is pulling against the force-feedback mechanism, which the tracking device 31 may determine to be a squeezing hand gesture. As another example, motion sensors may indicate that the glove is moving from one location to another within the physical space. For this example, the tracking device may determine that the user is making a panning hand gesture. The VR processor may produce (or generate) control signals that correspond to the manipulation of the virtual UID as a result of the performed hand gesture. Specifically, the VR processor determines whether the performed hand gesture corresponds to controlling one or more input of the virtual UID. For instance, the virtual UID may include a (virtual) button. The VR processor may determine that the user is pressing the button based on a hand gesture in which a finger is pressing towards the button.

In another embodiment, the VR processor may produce spatial state signals that correspond to movement of the virtual UID (e.g., position and orientation of the UID) according to a hand gesture in which the user is moving the virtual UID within the physical space. Similar to the spatial state signals produced by a (physical) UID 14, the state signals produced by the VR processor may be input signals to control a motion of the robot arm actuator 17. Thus, the system may produce one or more control signals derived from the spatial state signals, to control one or more components as described herein. In another embodiment, the spatial state signals may be produced by the force-feedback glove 20 based on sensor data from the sensors 28 (e.g., sensors 32). In this case, the glove may produce the state signals and transmit the signals to the VR processor.

The process 60 controls the component according to the hand gesture (at block 67). Specifically, the system may transmit the control signals produced by the VR processor to the components in order to perform one or more operations. For instance, in the case of a robotic arm 4, the control signals may cause the arm to move proportionally to the movement of the virtual UID (e.g., based on spatial state signals produced by the VR processor and/or by the force-feedback glove). The process 60 adjusts the applied forces according to the other hand gesture (at block 68). Specifically, the system may adjust the applied forces by the force-feedback mechanism 21 and/or the haptic-feedback mechanism 27, as described herein. For instance, when the virtual UID is squeezed, the force-feedback mechanism may be adjusted in order to apply more pulling force to counteract the squeezing hand gesture.

The process 60 determines whether the user has performed another hand gesture with the glove to manipulate the virtual UID (at decision block 69). For instance, the user may be continuing to perform a surgical procedure which involves controlling the same component. In one embodiment, the hand gesture may be the same or similar hand gesture that was previously performed, or a different hand gesture. If the user has performed another hand gesture (e.g., based on a tracking device's determination based on sensor data, as described herein), the process 60 returns to block 67 to control the component associated with the virtual UID according to the determined hand gesture.

If, however, another hand gesture to manipulate the virtual UID is not performed, the process 60 proceeds to determine whether the user is continuing to grasp the virtual UID (at decision block 70). Specifically, the tracking device determines whether the user is performing a hand gesture with the glove to release the virtual UID. For instance, the hand gesture may include extending one or more fingers away from the virtual UID, thereby releasing the virtual UID. If, however, the user continues to grasp the virtual UID, the process 60 returns to decision block 69. Otherwise, if the user releases the virtual UID the process 60 disengages the component from being controlled by the virtual UID (at block 71). In one embodiment, in response to the user releasing the virtual UID, the system disengages the component from being controlled. Specifically, the VR processor may transmit a disengagement signal to one or more controllers, indicating that the component is not to be controlled. In one embodiment, once disengaged, the component may hold its current position and orientation, thereby locking it in place. In one embodiment, once the virtual UID is released, it may hold its position and orientation, thus intuitively and naturally avoiding any unintended motion during disengagement (e.g. while ending the manipulation operation).

Some embodiments perform variations of the process 60. For example, the specific operations of the process may not be performed in the exact order shown and described. The specific operations may not be performed in one continuous series of operations and different specific operations may be performed in different embodiments. For example, the engagement of the component may be based on how the user is grasping the virtual UID. In particular, different hand gestures to grasp the virtual UID may engage different components. As an example, one pinching hand gesture to grasp the virtual UID with an index finger and a thumb may engage a first robotic arm. When, however, the user performs another pinching hand gesture with a middle finger and the thumb, the system may engage a second robotic arm to be controlled by the virtual UID.

In one embodiment, the system 1 may perform operations based hand gestures that are independent of virtual Ms. Specifically, upon determining that a hand gesture is performed, the system may perform an operation, such as controlling a component, as described herein. As an example, upon determining that the user is performing a hand gesture, such as bringing two fingers together (e.g., the index finger and the middle finger), the VR processor may engage a component to be controlled based on one or more additional hand gestures. To disengage, the user may perform a different hand gesture (e.g., bringing the two fingers apart). In one embodiment, the operations performed by independent hand gestures may be operations that may not be performed by virtual UIDs. For instance, the user may perform a particular hand gesture to select a virtual UID from several predefined virtual UIDs (e.g., making a swiping hand gestures from left to right).

Figure 5A:
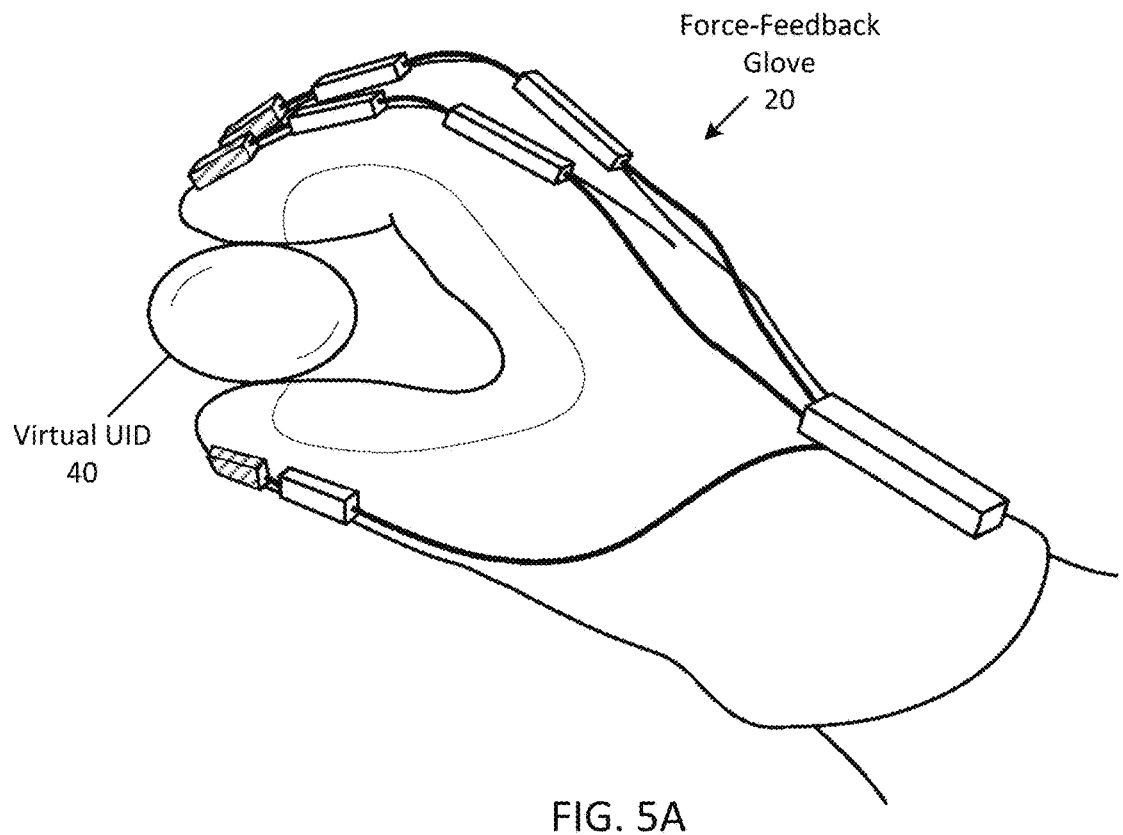
FIGS. 5A and 5B show a user who is wearing the force-feedback glove performing a hand gesture with the glove to manipulate a virtual UID in order to control a component of the surgical robotic system according to one embodiment.
Figure 5B:
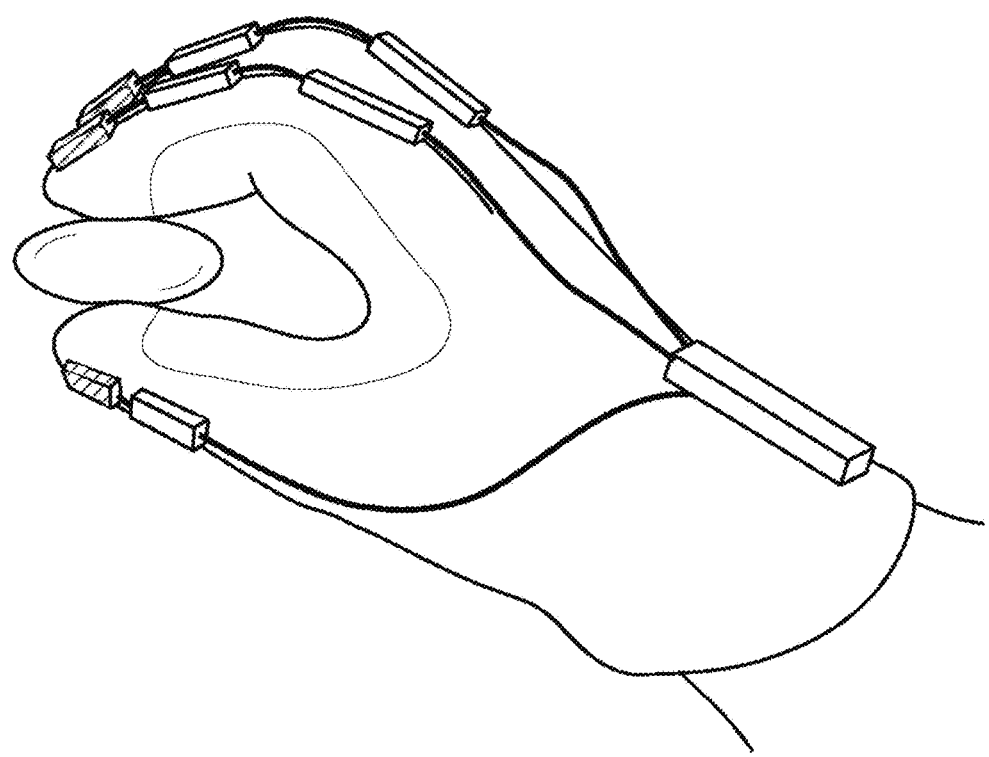

FIGS. 5A and 5B show a user who is wearing the force-feedback glove performing a hand gesture with the glove to manipulate a virtual UID in order to control a component of the surgical robotic system that is associated with the virtual UID according to one embodiment. Specifically, both figures show the glove 20 and a virtual UID 40.

As illustrated, the UID is an ellipsoid. As described herein, however, the UID may have any shape, and may have a similar shape as a physical UID, such as a handheld input device. Although illustrated, in one embodiment, the virtual UID may not be viewable by the user of the glove. Specifically, the surgical robotic system may not display an image of the virtual UID on a display (e.g., the user display 15) to the user. In one embodiment, the virtual UID may not need to be displayed, since the user may touch the physical representation of the virtual UID based on the applied forces of the force-feedback and haptic-feedback mechanisms.

FIG. 5A shows that the user is grasping the virtual UID with the force-feedback glove 20. In particular, the glove is making a grasping hand gesture in which each of the four fingers and the thumb are touching (a boundary of) the virtual UID. As described herein, in response to determining that the user is performing a hand gesture to grasp the UID, the system may engage a component associated with the virtual UID in order to enable the component to receive control signals in response to manipulation of the virtual UID. FIG. 5B shows that the user is manipulating the virtual UID with the glove in order to control a component. Specifically, the user is squeezing the virtual UID with one or more fingers, which may cause the component to perform a task. For instance, when the component is a grasper tool, squeezing the virtual UID may cause the tool to clamp down. Once released, however, the tool may return to an open state.

Figure 6:
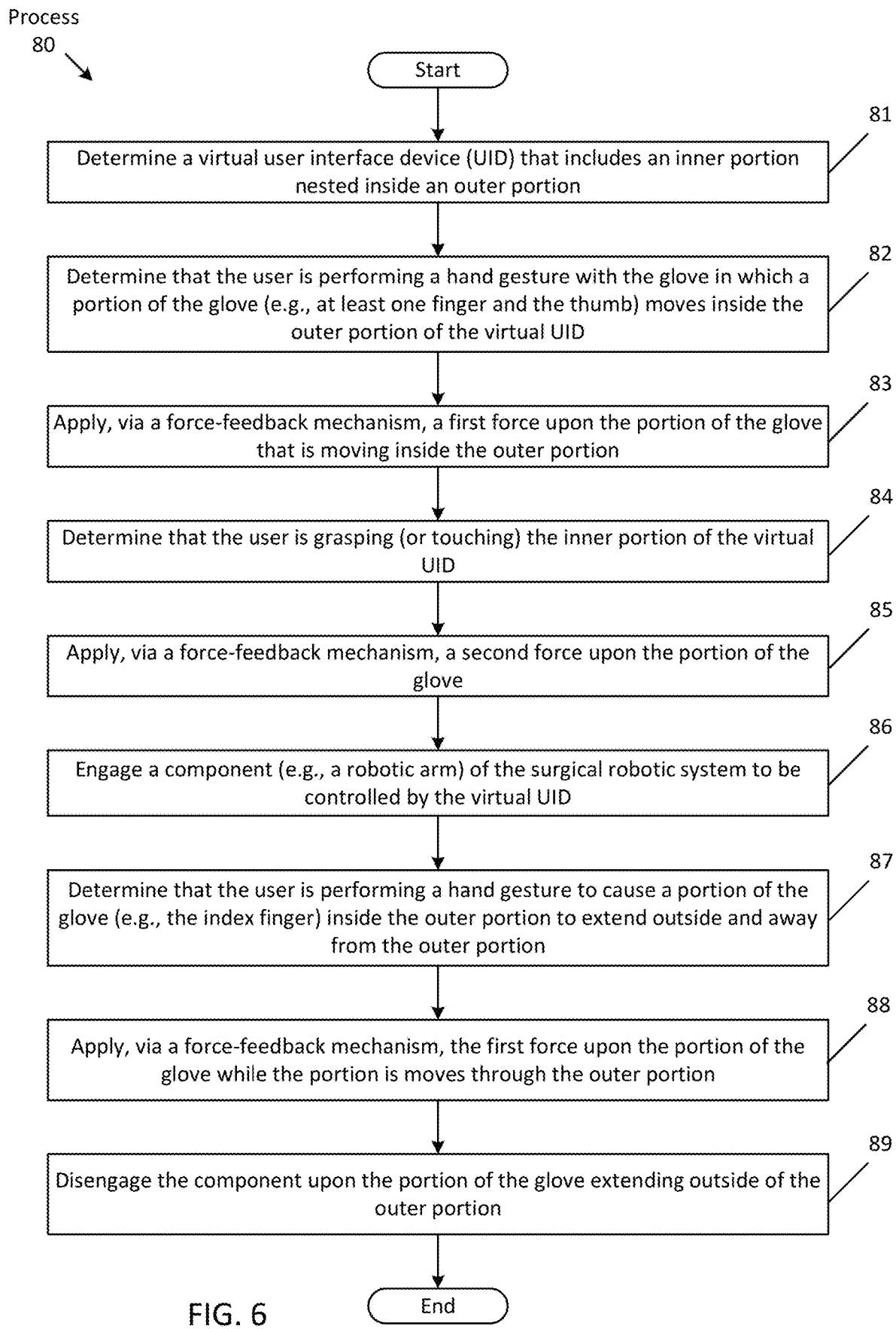
FIG. 6 is a flowchart of a process to engage and disengage a component of the surgical robotic system using a virtual UID according to one embodiment.

As described herein, a user may engage a component of the surgical robotic system by grasping or touching a virtual UID. In some embodiments, the system may provide an indication that the user is about to engage the component in order for the user to become ready to control the component with the virtual UID once engaged. To achieve this, the system may apply one or more forces upon the force-feedback glove, as the user performs a hand gesture to grasp the virtual UID. FIG. 6 provides a further explanation of such a design.

Figure 7A:
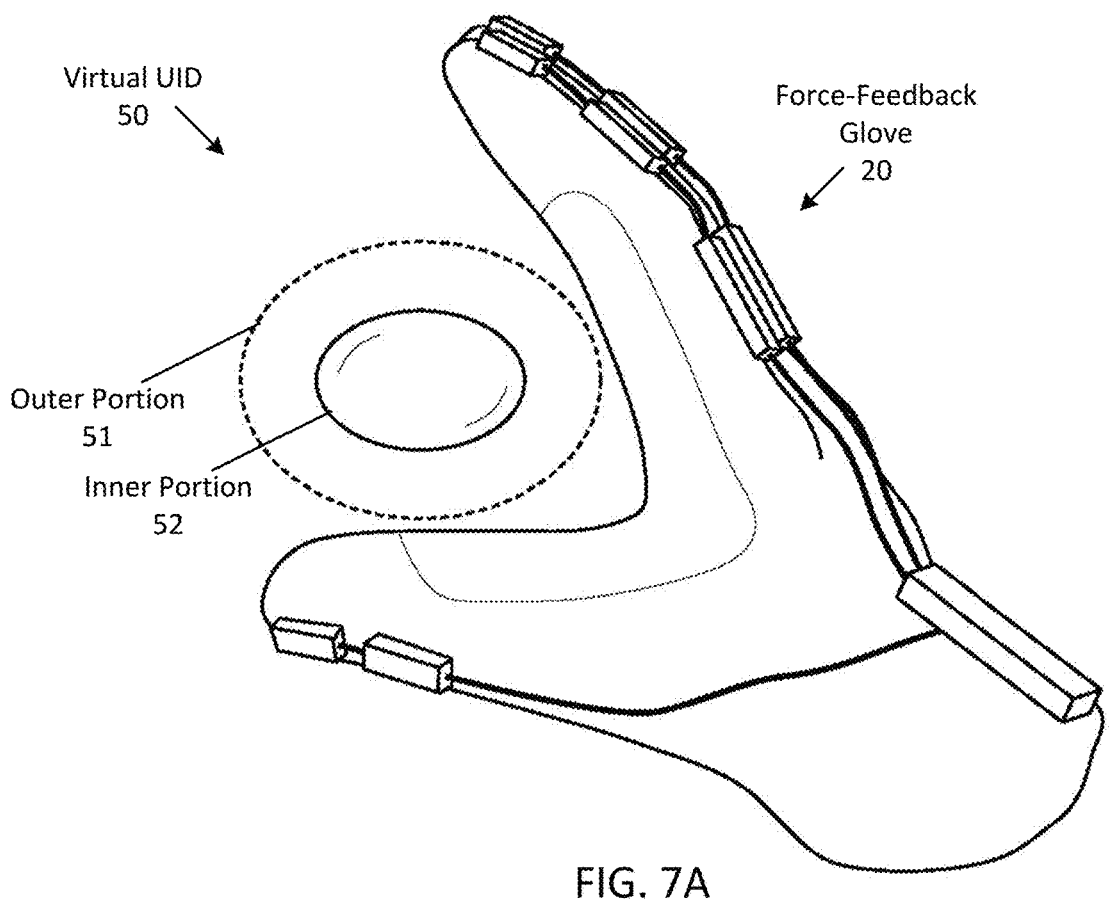
FIGS. 7A-7C shows several stages in which a user who is wearing the force-feedback glove performs hand gestures with the glove in order to engage and disengage a component of the surgical robotic system according to one embodiment.
Figure 7B:
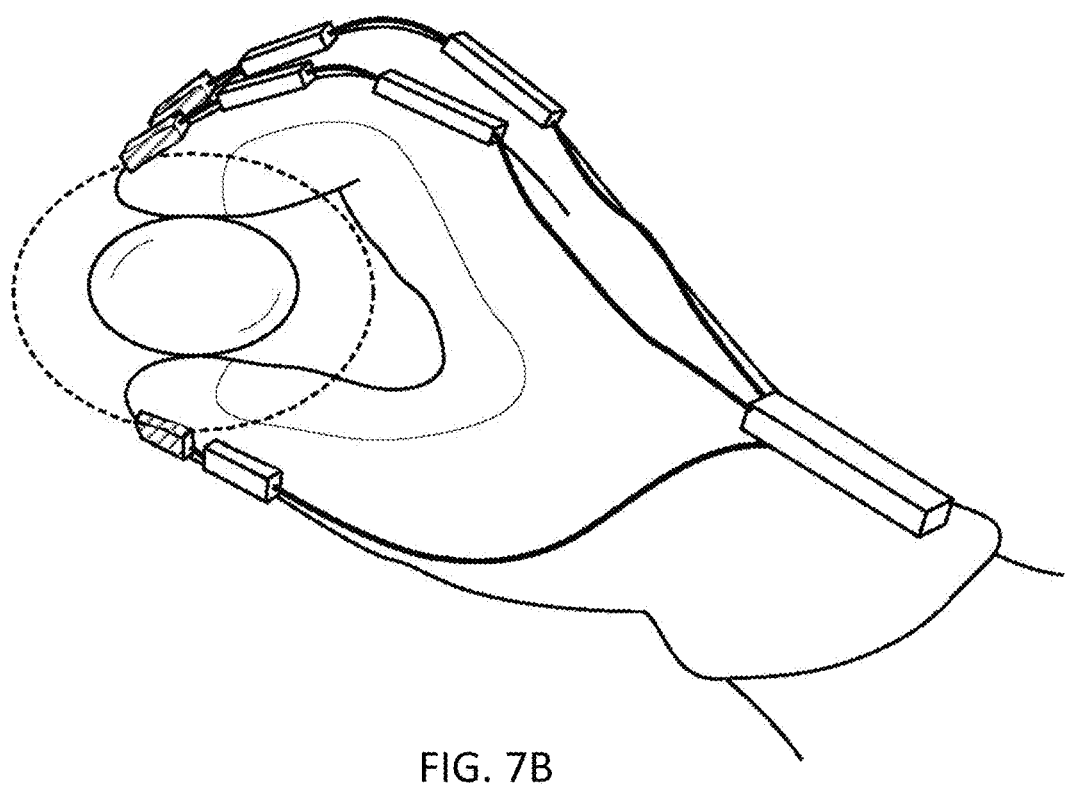
Figure 7C:
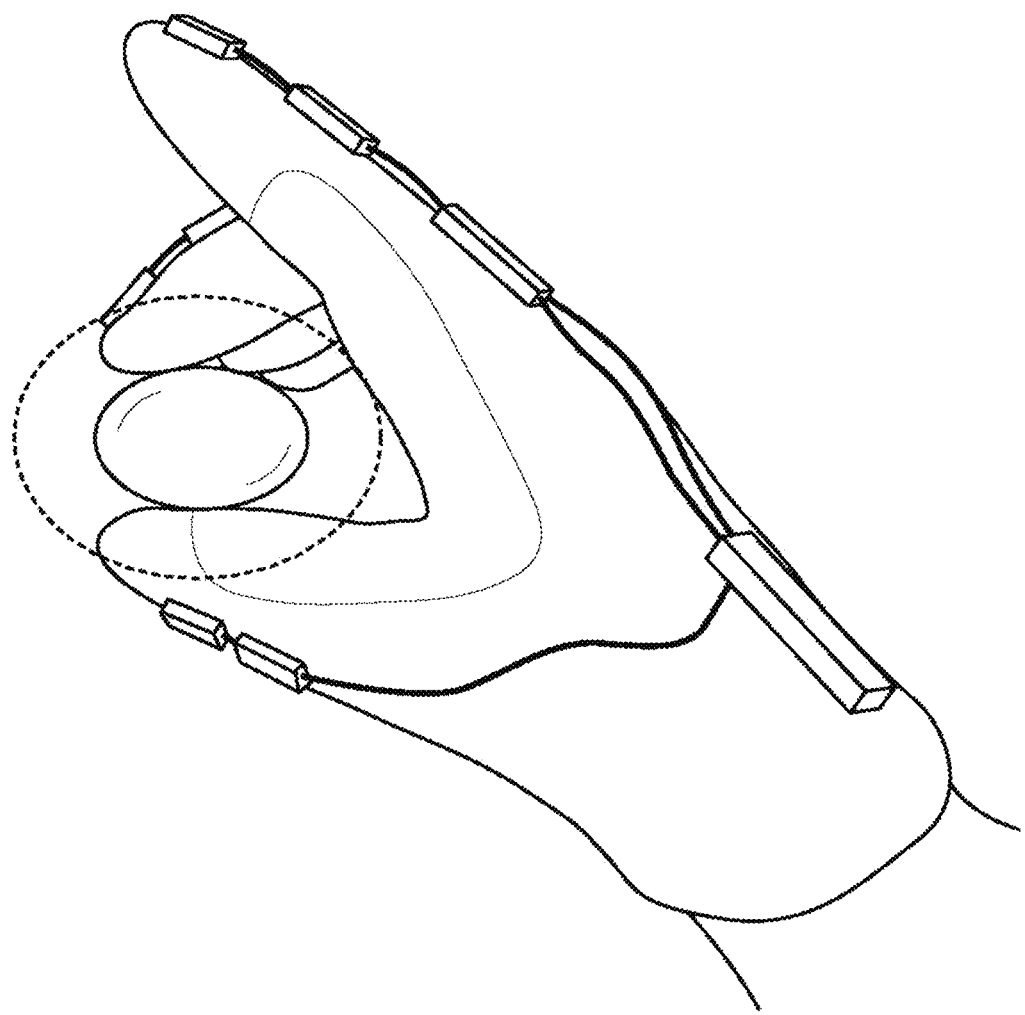

FIG. 6 is a flowchart of a process 80 to engage and disengage a component of the surgical robotic system using a virtual UID according to one embodiment. In one embodiment, the process 80 may be performed by the (e.g., VR processor 30 and/or tracking device 31 of the) surgical robotic system 1. In one embodiment, at least some of the operations described in process 80 may be the same or similar to at least some of the operations described in process 60 of FIG. 4. Accordingly, this figure will be described with reference to FIGS. 1-4. The process 80 begins by determining a virtual UID that includes an inner portion nested inside an outer portion (at block 81). For instance, as described in process 60, the determination may be based on a user-selection. In one embodiment, the virtual UID may be any virtual UID as described herein that is nested inside a boundary, between which the outer portion is formed. For example, the inner portion of the virtual UID may correspond to the virtual UID 40 illustrated in FIGS. 5A and 5B, while the outer portion may be a region that surrounds at least a portion of the virtual UID 40. This outer portion may have the same or similar shape as the inner portion, as illustrated in FIGS. 7A-7C. In another embodiment, the two portions may have different characteristics (e.g., based on the characteristics data). For instance, the outer portion may have a different shape, size, and texture than the inner portion. In one embodiment, the outer portion may extend from the inner portion by a predetermined distance (e.g., one inch).

The process 80 determines that the user is performing a hand gesture with the glove in which a portion of the glove (e.g., at least one finger and the thumb) moves inside the outer portion of the virtual UID (at block 82). For instance, the hand gesture may be a grasping gesture in which the user is attempting to grasp the virtual UID with an index finger and the thumb. More specifically, the user is attempting to grasp the inner portion of the virtual UID. Thus, the system may determine that the portion of the glove is moving inside the outer portion, while the user is performing a hand gesture to grasp the inner portion. The process 80 applies, via the force-feedback mechanism, a first force upon the portion of the glove that is moving inside the outer portion (at block 83). For instance, once the VR processor 30 determines that the portion of the glove is moving inside the outer portion, the processor may transmit control signals to the glove in order for the force-feedback mechanism 21 to apply at least one force upon the portion. In one embodiment, the applied force may reduce the movement of the user's hand, but may not entirely prevent the movement. Thus, in order to continue moving, the user may need to exert more force than would otherwise be required (e.g., when outside the outer portion).

The process 80 determines that the user is grasping (or touching) the inner portion of the virtual UID (at block 84). For example, when the portion of the glove that entered the outer portion was an index finger and thumb, the tracking device may track the finger and thumb while they move inside the outer portion. The system may determine that the finger and thumb are grasping the inner portion, once the finger and thumb reach the inner portion (e.g., reach a boundary of the inner portion). The process 80 applies, via the force-feedback mechanism, a second force upon the portion of the glove that is grasping the inner portion (at block 85). In one embodiment, the second force may represent the physical representation of the virtual UID, as described herein. Thus, the second force may be a stronger force than the first force. For instance, the second applied force may further reduce or even prevent additional movement by the user's hand (e.g., additional grasping movement). The process 80 engages the component (e.g., a robotic arm) of the surgical robotic system to be controlled by the virtual UID (at block 86). In one embodiment, to control the component, the user may manipulate the inner portion of the virtual UID, as described herein. In another embodiment, the outer portion may mirror any manipulation of the inner portion. For instance, if the user were to move the virtual UID in order to cause the component to move, the outer portion may mirror the inner portion's movements.

The process 80 determines that the user is performing a (second) hand gesture to cause a portion of the glove (e.g., the index finger) that is inside the outer portion to extend outside and away from the outer portion (at block 87). For instance, the tracking device may determine that the user is performing a hand gesture in which one finger, such as the index finger is moving away from the inner portion and attempting to extend the finger outside the outer portion, while at least some of the other fingers continue to grasp the virtual UID. The process 80 applies, via the force-feedback mechanism, the first force upon the portion of the glove while it moves through the outer portion (at block 88). Specifically, the force-feedback mechanism may apply the same or similar force upon the portion of the glove that is moving away from the inner portion, but still inside the outer portion in response to determining that the user is performing the second hand gesture. Thus, the force-feedback mechanism may apply the same or similar force to any portion of the glove that is inside the outer portion. In one embodiment, the system may apply the force until the portion of the glove exits out from the outer portion. The process 80 disengages the component upon the portion of the glove extending outside of the outer portion (at block 89). This allows the user to disengage the component, while continuing to grasp or touch the inner portion of the virtual UID. As a result, the user may disengage, while keeping the component in a particular state. For instance, before disengaging, the user may manipulate the inner portion to control the component to perform an operation. As an example, when the component is a grasper, the user may squeeze the virtual UID in order to control the grasper to clamp down. After which, the user may disengage by moving one finger outside the outer portion, while continuing to squeeze the UID with the other fingers. As a result, the grasper will continue to claim down after disengaging.

Some embodiments perform variations of the process 80. For example, the specific operations of the process may not be performed in the exact order shown and described. The specific operations may not be performed in one continuous series of operations and different specific operations may be performed in different embodiments.

FIGS. 7A-7C shows several stages in which a user who is wearing the force-feedback glove performs hand gestures with the glove in order to engage and disengage a component of the surgical robotic system according to one embodiment. Specifically, each of the figures illustrate an interaction between a virtual UID 50 and the force-feedback glove 20. As shown, the virtual UID 50 includes an inner portion 52 that is nested inside an outer portion 51. In one embodiment, the inner portion 52 is the same as the virtual UID 40 illustrated in FIGS. 5A and 5B. FIG. 7A shows that no portion of the force-feedback glove 20 is inside the outer portion of the virtual UID. As a result, the (force-feedback mechanism 21 of the) glove may not be applying any forces. In one embodiment, this figure shows a beginning of a hand gesture in which the user is attempting to grasp the virtual UID.

FIG. 7B shows that the user is grasping the inner portion 52 of the virtual UID 50. In one embodiment, the force-feedback mechanism may apply a first force while the user is making a grasping hand gesture towards the inner portion. Upon making contact with the inner portion the mechanism may apply a second force that is stronger than the first in order to provide a feeling that the user is now grasping the virtual UID. FIG. 7C shows that the user has extended the index finger out of the outer portion of the virtual UID. As described herein, once performed the system may disengage the component associated with the virtual UID. In one embodiment, any portion of the glove (e.g., any finger) may be used to disengage the component by performing this gesture.

As previously explained, an embodiment of the disclosure may be a non-transitory machine-readable medium (such as microelectronic memory) having stored thereon instructions, which program one or more data processing components (generically referred to here as a "processor") to perform any of the operations described herein. In other embodiments, some of these operations might be performed by specific hardware components that contain hardwired logic. Those operations might alternatively be performed by any combination of programmed data processing components and fixed hardwired circuit components.

While certain embodiments have been described and shown in the accompanying drawings, it is to be understood that such embodiments are merely illustrative of and not restrictive on the broad disclosure, and that the disclosure is not limited to the specific constructions and arrangements shown and described, since various other modifications may occur to those of ordinary skill in the art. The description is thus to be regarded as illustrative instead of limiting.

In some embodiments, this disclosure may include the language, for example, "at least one of [element A] and [element B]." This language may refer to one or more of the elements. For example, "at least one of A and B" may refer to "A," "B," or "A and B." Specifically, "at least one of A and B" may refer to "at least one of A and at least one of B," or "at least of either A or B." In some embodiments, this disclosure may include the language, for example, "[element A], [element B], and/or [element C]." This language may refer to either of the elements or any combination thereof. For instance, "A, B, and/or C" may refer to "A," "B," "C," "A and B," "A and C," "B and C," or "A, B, and C."

What is claimed is:

1. A surgical robotic system comprising:
   a robotic arm;
   a glove configured to be worn on a hand of a user and including a force-feedback mechanism;
   a tracking device;
   a processor; and
   memory having instructions which when executed by the processor causes the system to
      determine that the user is performing a hand gesture with the glove to grasp a virtual user input device (UID) based on the tracking device;
      in response to the user grasping the virtual UID,
         apply, via the force-feedback mechanism, a force upon the glove that corresponds to a physical representation of the virtual UID; and
         engage the robotic arm to be controlled by the virtual UID.

2. The surgical robotic system of claim 1, wherein the hand gesture is a first hand gesture, wherein the memory has further instructions to
   determine that the user is performing a second hand gesture with the glove to release the virtual UID based on the tracking device; and
   in response to the user releasing the virtual UID, disengage the robotic arm from being controlled by the virtual UID.

3. The surgical robotic system of claim 1, the hand gesture is a first hand gesture, wherein the memory has further instructions to
   determine that the user is performing a second hand gesture with the glove to manipulate the virtual UID based on the tracking device; and
   control the robotic arm according to the second hand gesture.

4. The surgical robotic system of claim 3, wherein the second hand gesture is at least one of a squeezing motion that represents squeezing the virtual UID or a hand movement that represents moving the virtual UID.

5. The surgical robotic system of claim 1, wherein the glove includes a haptic feedback mechanism, wherein the memory has further instructions to apply, via the haptic feedback mechanism and upon the glove grasping the virtual UID, a plurality of forces that represent a surface of the physical representation of the virtual UID.

6. The surgical robotic system of claim 1, wherein the force is a first force and the virtual UID comprises an inner portion that is nested inside an outer portion, wherein the memory has further instructions to determine that a portion of the glove is moving inside the outer portion; and in response to determining that the portion of the glove is moving inside the outer portion, apply, via the force feedback mechanism, a second force upon the portion of the glove.

7. The surgical robotic system of claim 6, wherein the first force is stronger than the second force.

8. The surgical robotic system of claim 6, wherein in response to the user grasping the inner portion the force feedback mechanism is arranged to apply the first force that corresponds to the physical representation of the virtual UID.

9. The surgical robotic system of claim 8, wherein the hand gesture is a first hand gesture, wherein the memory has further instructions to determine that the user is performing a second hand gesture with the glove to cause another portion of the glove that is inside the outer portion to extend outside and away from the outer portion based on the tracking device, while continuing to grasp the inner portion; and in response to determining that the user is performing the second hand gesture, apply, via the force-feedback mechanism, the second force upon the other portion of the glove until it exits the outer portion, and disengage the robotic arm from being controlled by the virtual UID upon the other portion of the glove exiting the outer portion.

10. The surgical robotic system of claim 9, wherein the other portion of the glove is at least one finger.

11. The surgical robotic system of claim 1, wherein the virtual UID has a location within a physical space that is proximate to a palmar side of the glove and is stationary with respect to the glove such that the virtual UID mirrors movements of the glove within the physical space.

12. The surgical robotic system of claim 1, wherein the robotic arm is a first robotic arm, wherein the surgical robotic system comprises a second robotic arm, wherein the instructions to determine that the user is grasping the virtual UID comprises instructions to determine a first finger and the thumb are grasping the virtual UID, wherein the memory has further instructions to determine that a second finger and the thumb are grasping the virtual UID based on the tracking device; and in response to the user grasping the virtual UID with the second finger, engage the second robotic arm to be controlled by the virtual UID.

13. A method performed by a programmed processor of a surgical robotic system that includes a glove configured to be worn on a hand of a user and a robotic arm, the method comprising:

determine that the user is grasping a virtual user input device (UID) with the glove;

in response to the user grasping the virtual UID, apply, via a force-feedback mechanism of the glove, a force upon the glove that corresponds to a physical representation of the virtual UID, and engage the robotic arm to be controlled by the virtual UID.

14. The method of claim 13, wherein the hand gesture is a first hand gesture, wherein the method further comprises determining that the user is performing a second hand gesture with the glove to release the virtual UID; and in response to the user releasing the virtual UID, disengaging the robotic arm from being controlled by the virtual UID.

15. The method of claim 13, wherein the hand gesture is a first hand gesture, wherein the method further comprises determining that the user is performing a second hand gesture with the glove to manipulate the virtual UID; and controlling the robotic arm according to the second hand gesture.

16. The method of claim 15, wherein the second hand gesture is at least one of a squeezing motion that represents squeezing the virtual UID or a hand movement that represents moving the virtual UID.

17. The method of claim 13, wherein the force is a first force and the virtual UID comprises an inner portion that is nested inside an outer portion, the method further comprises determining that a portion of the glove is moving inside the outer portion; and in response to determining that the portion of the glove is moving inside the outer portion, apply a second force upon the portion of the glove.

18. The method of claim 17, wherein the first force is stronger than the second force.

19. The method of claim 17, wherein grasping the virtual UID comprises grasping the inner portion of the virtual UID.

20. The method of claim 19, wherein the hand gesture is a first hand gesture, wherein the method further comprises determining that the user is performing a second hand gesture with the glove to cause another portion of the glove that is inside the outer portion to extend outside and away from the outer portion, while continuing to grasp the inner portion; and in response to determining that the user is performing the second hand gesture, applying the second force upon the other portion of the glove unit it exits the outer portion, and disengaging the robotic arm from being controlled by the virtual UID upon the other portion of the glove exiting the outer portion.

* * * * *